United States Patent [19]

Taller et al.

[11] Patent Number: 4,817,593

[45] Date of Patent: * Apr. 4, 1989

[54] PROCESS FOR PREPARATION OF POLYURETHANE CONDOMS

[75] Inventors: Robert A. Taller; Charles W. McGary, Jr., both of Centerville, Ohio

[73] Assignee: Deseret Medical Inc., Franklin Lakes, N.J.

[*] Notice: The portion of the term of this patent subsequent to Aug. 4, 2004 has been disclaimed.

[21] Appl. No.: 43,061

[22] Filed: Apr. 27, 1987

Related U.S. Application Data

[60] Division of Ser. No. 903,822, Sep. 2, 1986, Pat. No. 4,684,490, Continuation of Ser. No. 555,861, Nov. 28, 1983, abandoned.

[51] Int. Cl.$^4$ .......................... A61F 13/00; A61F 5/44
[52] U.S. Cl. ..................................... 128/844; 604/349
[58] Field of Search ................... 128/132 R; 604/347–353

[56] References Cited

U.S. PATENT DOCUMENTS

| | | | |
|---|---|---|---|
| 2,814,834 | 12/1957 | Hess et al. | 18/58.6 |
| 3,098,755 | 7/1963 | Barth et al. | 117/33 |
| 3,105,062 | 9/1963 | Graham | 260/75 |
| 3,136,417 | 6/1964 | Clinch | 604/349 |
| 3,148,234 | 9/1964 | Velonis et al. | |
| 3,148,235 | 9/1964 | Velonis et al. | |
| 3,520,305 | 7/1970 | Davis | 604/349 |
| 3,553,308 | 1/1971 | Kobayashi et al. | 264/305 |
| 3,846,378 | 11/1974 | Griswold | 260/77.5 |
| 4,100,309 | 7/1978 | Micklus et al. | 427/2 |
| 4,119,094 | 10/1978 | Micklus et al. | 128/132 R |
| 4,434,126 | 2/1984 | McGary et al. | 264/303 |
| 4,576,156 | 3/1986 | Dyck et al. | 128/132 R |
| 4,684,490 | 8/1987 | Taller et al. | 264/296 |

FOREIGN PATENT DOCUMENTS

| | | | |
|---|---|---|---|
| 33958 | 10/1973 | Japan | 604/349 |
| 752171 | 8/1954 | United Kingdom. | |

OTHER PUBLICATIONS

Advances in Polyurethane Technology Buist et al., Maclaven & Sons London, U.K., 1968—Reference book—Available from Library of Levis W. Jacobs Room 2-10 D06.

"Elastomers, A Desk Type Data Bank", International Plastics Selector, Inc., San Diego, 92126, 1980 pp. 93–156; 427–448.

Defensive Publication T856013-Richard D. Samson-Published 11/12/68.

Primary Examiner—C. Fred Rosenbaum
Assistant Examiner—J. L. Kruter
Attorney, Agent, or Firm—Robert P. Grindle

[57] ABSTRACT

A process of making a polyurethane condom which comprises providing an organic solvent solution of a polyurethane, a single dipping of a condom form or mold into the polyurethane solution, raising the form from solution and allowing the resultant deposited film to cure at elevated temperatures, thereby forming the condom.

8 Claims, 1 Drawing Sheet

PROCESS FOR PREPARATION OF POLYURETHANE CONDOMS

This is a continuation of Ser. No. 06/555,861, filed Nov. 28, 1983 now abandoned. This is a division, of application Ser. No. 903,822, filed 9/2/86 now U.S. Pat. No. 4,684,4.

The instant invention relates to a novel process for making a polyurethane condom using a dip-molding technique which requires only one dip of a condom form or mold into a polyurethane solution. Cure of the polyurethane film mold is effectuated by means of heat once the form is raised from the polyurethane solution. Neither curing agents, coagulation agents or other traditional means of causing polymers to cure are necessary.

Heretofore, natural rubber latex compositions have been used to make condoms by both dip-molding and emulsion coagulation techniques. Polyurethane compositions have also been used to make condoms by solution dip molding techniques. The polyurethane condom methodology, however, has been unsatisfactory, requiring multiple complex processing procedures in the use of such multiple steps. In addition, the polyurethane coating system of the prior art is inherently unstable rendering the system commercially unfeasible.

Prior Art dip-molding techniques have not been completely acceptable in producing a condom having the requisite properties for a high quality synthetic rubber condom product by means of a simple one-dip process. Latex rubber condoms suffer from undesirable film thickness and inherent insulating characteristics which results in inefficient heat transfer. The result is a reduction in sensory perception to the user.

Emulsion technology is presently the primary technique for producing natural rubber condoms. Generally, the elastomeric resin (rubber) material is present in aqueous emulsion. The condom mold (or form) is coated with a coagulation agent and the mold is dipped into the aqueous based emulsion whereupon the coagulation agent destabilizes the emulsion causing the emulsion to film out on the mold. Coatings can also be applied via a non-coagulant multiple dip process. The resultant film is then leached to remove the water soluble coagulation salts, dried and cured.

Emulsion techniques have also been used with polyurethane polymer compositions which when utilizing coagulation agents suffer from several undesirable features. Condoms must be thin enough to provide excellent heat transfer and sensory perception to the user, must be free from pinholes and potential leakage and must be mechanically strong but flexible. Condoms produced by emulsion techniques do not provide all of these requisites for several reasons. Thickness of the condom is controlled by several factors; for example, the concentration of the emulsion, the amount of the coagulant, the dwell time of the coagulant coated condom mold in the emulsion and the rate of withdrawal of the mold from the emulsion. An increase in any of these factors produces a thicker film. Regardless of attempts to properly control these factors, the tip of the condom, which is the portion where thinness is most desirable, is invariably thicker than the remainder of the condom for the simple reason that it is the last portion to be withdrawn from the emulsion. Uniform thickness is therefore impracticable with this technique.

U.S. Pat. No. 3,553,308 discloses a method of making a polyurethane condom of less than 50 microns by alternately dipping from 3 to 6 times, at a controlled speed of 300–500 mm/min, a condom mold first in polyurethane prepolymer solution and then in a curing solution, said prepolymer having an NCO/OH ratio of more than 1/1, an average molecular weight of about 500 to 5,000, a viscosity of about 0.7 to 20 cps and a concentration of about 1 to 80 weight percent. The curing agent is a polyamine used in a concentration of about 0.01 to 10 weight percent. This method involves a series of dipping and curing steps. This patent involves preparing a prepolymer solvent solution and a separate curing agent solvent solution. The prepolymers of this reference are not particularly stable and tend to react with moisture from the environment causing increases in viscosity due to gelation. Thus, pot-life of the polyurethane solutions of this reference would be expected to be limited. The production of amine salts in the curing agent bath are also a known undesirable effect present in methods such as this.

Polyurethanes, in contrast to natural rubber condoms, are resistant to petroleum based lubricants such as Vaseline jelly and they provide longer packaged shelf-life since they have better thermal and oxidative (ozone) stability than natural rubber. It is apparent that there is a need for a process by which a high quality polyurethane condom can be made without the need for curing agents or coagulants and which produces a pinhole-free condom of uniform thickness without jeopardizing flexibility or mechanical integrity.

The instant process does not suffer from the disadvantages of the traditional solution or emulsion dip-molding techniques and provides an inexpensive, simplified means of producing a condom with uniform thickness and excellent mechanical properties. According to the invention, the condom form is dipped once into an organic solvent solution of a polyurethane prepolymer and raised at a controlled speed. The deposited film is then cured at elevated temperatures of about 130° to about 175° C. and cooled to about 50°-60° C., at which time an integral cuff is formed at the base of the condom by rolling up the film on the mold, starting from the base, to a desired position from the condom tip. Cure time of the polyurethane condom can range from about 20 minutes to about 40 minutes, depending upon cure temperature and formulation of the polyurethane prepolymer solution. Thirty minutes is the preferred cure time. The formation of the integral cuff at the base of the condom is critical to the final product since it provides the starting place for rolling and packaging. The cuff must bind to the condom wall before a dry or wet lubricant is applied.

DEFINITIONS

The following terms are used in describing the invention.

The term segmented polyurethanes as used herein includes both polyurethanes wherein the hard segment is formed by a single polyisocyanate monomer and polymers in which the hard segment is formed by two or more isocyanate monomers interconnected by short chain diols.

The invention polyurethanes and long chain diols are said to be amorphous or non-crystalline when they are essentially non-crystalline and they do not crystallize appreciably at room temperature.

Percent hard segment is the percent isocyanate plus any extender based on the total weight of the polymer.

Tear is Die C tear or slit and measured in accordance with ASTM D624-73, D1004-64, ANSI/ASTM D1938-67.

Tensile, Modulus and elongation are measured in accordance with ASTM D638-80, D882-80a.

Initial tensile set as used herein is the percent set as determined immediately after testing elongation in accordance with ASTM D412-68 by measuring the percent increase between 1 inch markings without allowing time for recovery. [Due to the tendency of the physical properties of a polyurethane to change with time, the values used herein are equilibrium values and are generally reached 3 to 4 weeks after manufacture.]

Molecular weight per cross-link ($M_c$) is calculated as set forth in POLYURETHANE CHEMISTRY AND TECHNOLOGY, Saunders and Frisch, Robert E. Krieger Publishing Co., Huntington, N.Y. (1978) p. 266.

More particularly the instant invention concerns a process for making the polyurethane condoms with a uniform thickness of about 1.5 to about 4.0 mils which comprises:

(a) providing a solvent solution of a polyurethane polymer or prepolymer, said polymer or prepolymer being the reaction product of a polyisocyanate with at least one long chain polyol, said polyol being amorphous at room temperature and having an average molecular weight of about 500 to about 5,000 and an hydroxy number of about 225 to about 22.4, said polyisocyanate having an NCO/OH ratio of about 0.95/1 to about 1.1/1; and most preferably about 1.0/1 to about 1.05/1;

(b) dipping a mold on which a condom is to be fashioned into the polyurethane solution and withdrawing the mold from the solution;

(c) heating the deposited polyurethane film to effectuate curing and removing the cured polyurethane condom from said mold.

IN THE DRAWINGS

FIG. 1 is a longitudinal view partially in section of one embodiment of the invention.

DETAILED DESCRIPTION OF THE INVENTION

Figure 1:
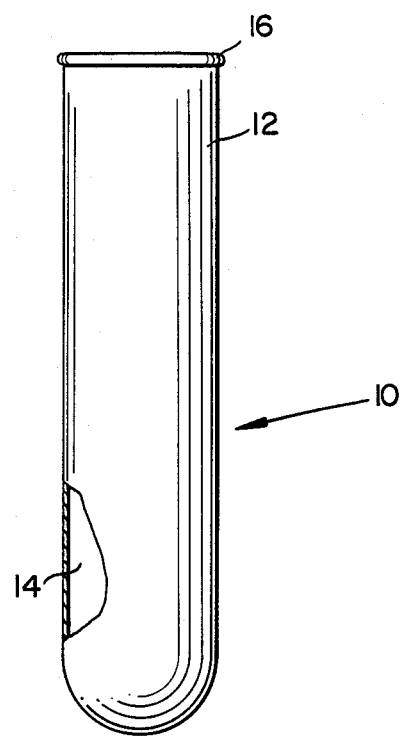

Referring to the drawings in which like reference numbers refer to like parts throughout the several views thereof, FIG. 1 shows a longitudinal view of an embodiment 10 of the condom of the invention having a tubular body 12 formed of the thin wall 14. Integrally formed on the top edge of wall 14 is integral cuff 16.

The condoms produced by the instant process have the following properties:

(i) a 100% tensile modulus of less than about 150 psi
(ii) a tensile strength at break of at least about 3,000 psi
(iii) an elongation at break of at least about 500%
(iv) A tensile set after 1 minute of less than about 40
(v) a slit tear value of at least about 20 pli
(vi) a die c tear value of about 90 to about 130 pli.

One of the important advantages of the instant process concerns the approximate uniform thickness of the condom wall. It is necessary to provide as thin a condom wall as possible without jeopardizing the mechanical properties of the condom or risking the formation of pinholes. Thus, a delicate balance must be maintained between the thickness of the condom wall and such properties as tensile strength, elongation and tear resistance.

The thickness of the condom should be between about 1.5 and about 4.0 mils and preferably between about 2.2 and about 2.8 mils. The most preferred thickness is 2.5 mils±0.3. The average standard deviation of wall thickness as measured between any two points on the condom should not be greater than about ±0.3 mils, preferably about ±0.2 mils and most preferably about ±0.15 mils. The uniformity of wall thickness throughout the polyurethane condom provides improved heat transfer when donned by the user and hence improved sensory perception.

The polyurethanes of the instant invention do not require a separate curing bath as do those of the prior art. Rather, the instant process requires the condom mold to be dipped once in the polyurethane solution. Withdrawal need not be performed at the high speed as disclosed in the prior art (see U.S. Pat. No. 3,553,308) where several dips in both the polymer and curing solutions were required for thickness.

The mold upon which the condoms of the instant process are to be fashioned is dipped into the polyurethane solution and generally withdrawn from the solution at a rate of about 16 to about 90 cm/min and preferably at a rate of about 20 to about 35 cm/min. The preferred rate of raising the condom form from the polyurethane solution is dependent to a large degree on the polyurethane prepolymer formulation chosen. The desired rate of withdrawal is easily adjusted and determined by routine experimentation by the reasonably skilled person. The dwell time of the condom form in the polyurethane prepolymer solution generally varies from about 20 to about 70 seconds and preferably about 30 to about 60 seconds prior to withdrawal.

Once withdrawn from solution, the polyurethane condoms deposited on the dipped forms are allowed to air dry and then cured at elevated temperatures. Again, cure temperatures and curing times will vary according to the polyurethane prepolymers chosen, but generally the temperatures for curing will be between about 130° to about 175° C. for a duration of about 20 to about 40 minutes.

The instant process thus provides a faster, more efficient means of making polyurethane condoms by eliminating subsequent dipping and curing steps conventionally used in the art. This advantage allows for increased continuity and cost savings on the assembly line.

The polyurethanes used in the process of the instant invention are segmented block copolymers constituted by alternating sequences of hard rigid segments and soft, flexible segments.

One discussion of polyurethane chemistry is found in *Polymer Science and Technology*, "Polymers in Medicine and Surgery," Kronenthal et al, Vol. 8, pp. 45-75. Generally, the hard and soft segments in these polymers are incompatible such that microphase separation or domain formation occurs. Where the soft segment is dominant, the hard segment domains serve as physical cross links and gives the polymers elastomeric properties.

In the polymers used in the instant process the hard segment and degree of cross-linking are balanced within the ranges of approximately 14 to 25% hard segment and approximately 5,000 to 30,000 molecular weight per cross-link ($M_c$). Preferred polymers in accordance with the invention contain units of polyester and/or polyether diols providing a soft segment average molecular weight in the range of approximately 500 to 5000. Still more preferred polymers contain approximately 16 to 20% hard segment and 8,000 to 25,000 $M_c$. Generally, the polyurethane polymers used in the inventive process provide a Shore A durometer hardness of about 35 to 60 and preferably 40 to 55.

A number of problems are encountered in achieving low modulus and low set in a polyurethane elastomer. Although polymers containing greater than 25% hard segment may be non-crystalline and have low set, due to the rigidity caused by the high amount of hard segment in these polymers, they are unsatisfactory for applications where very low modulus is required. Accordingly, in the present invention the amount of hard segment is limited to a maximum of 25% by weight. However, when the hard segment is limited to 25% maximum there is insufficient domain formation or physical cross-linking for low set, e.g., some of these polymers have poor elastic memory and tend to creep and cold flow when extended. This is particularly true where the long chain diol is highly amorphous as in the instant invention. For this reason, a degree of chemical cross-linking is relied upon in the polymers to fix the polymeric matrix and thereby improve set and overall elasticity. Thus, in accordance with the invention softness is obtained in an essentially non-crystalline polymer with low set by a combination of physical and chemical cross-linking.

Another problem encountered in arriving at a very low modulus polyurethane elastomer is that in many cases the long chain diol incorporated in the polymer gradually crystallizes and produces a drastic increase in the modulus. By cross-linking the polymer it is possible to lock the diol into an essentially non-crystalline conformation and obtain modulus stability in a polymer which would otherwise crystallize into a rigid, nonelastic sheet. Thus, in the first instance physical and chemical cross-linking are balanced in the inventive polymers to obtain elastic properties in a low modulus polymer. In the second instance, principally chemical cross-linking but in a related sense also physical cross-linking is used to reduce crystallization. This enables one to build a soft polyurethane elastomer from polyisocyanates and diols that provide the desired low modulus (as well as the desired elongation, tear and tensile in the preferred case) and, at the same time, avoid high set and crystallization due to the high molecular weight diol.

The desired properties are also obtained through selecting a long chain diol or combination of diols which tend to crystallize little at ambient temperatures in the polymer. The long chain diols of the instant process must be amorphous at room temperature and hence generally have a low melting point. For example, polyethylene/butylene adipate polyester polyols of 2000–3000 molecular weight have a melting point range of about 23° to about 30° C. These polyols are particularly useful in the instant process.

Thus, the present invention can be viewed as building sufficient physical and chemical cross-linking in a polyurethane so as to obtain elastomeric properties, minimize crystallization, and reduce set. In addition, by also selecting a diol or combination of diols which remains amorphous at ambient temperatures or has a low affinity for crystallization in the polymers at those temperatures, it is possible to achieve low set, minimize crystallization and simultaneously maintain a low modulus. Where the diol component is more crystalline, the degree of crosslinking required to minimize its crystallization often produces a modulus too high to be useful in making condoms.

Representative polyurethane polymers comprise about 13 to about 23% isocyanate, about 70 to about 84% long chain diol and about 0.75 to about 6% of a cross-linking agent. While a short chain diol extender is not necessarily present, when it is present it is used in an amount of about 0.5 to about 3.0%.

In preferred polymers there is a high degree of incompatibility between the hard and soft segments such that there is a strong affinity within the hard and soft segments which leads to segmentation or domain formation. Where the polyisocyanate is aromatic or alicyclic and the long chain diol is aliphatic, this occurs quite readily.

Representative polyisocyanates useful in the present invention include aromatic and alicyclic diisocyanates such as 4,4'-diphenyl methane diisocyanate (MDI), toluene diisocyanate (TDI), isophorone diisocyanate (IPDI), methylene bis(4-cyclohexyl)diisocyanate (HMDI), etc. Of these MDI and HMDI are particularly preferred. In addition to the aforementioned diisocyanates, the invention can also be practiced using aromatic and cycloaliphatic triisocyanates and tetraisocyanates.

It has been found that 4,4'-diphenyl methane diisocyanate (MDI) is particularly desirable for use in the formation of the polyurethane polymers used in the instant process. Using this polyisocyanate provided polyurethane films which have 100% modulus of about 120 or less and a tear propagation of about 24 to about 50 pli.

Various extenders may optionally be used in the present invention. In the most typical case the extender is a short chain diol such as a straight or branched chain diol having two or six carbon atoms in the main chain, e.g., ethylene glycol, propylene glycol, 1,4 butanediol, neopentyl glycol, etc. or an alicyclic glycol having up to 10 carbon atoms, e.g., 1,4 cyclohexane diol, 1,4 dimethylol cyclohexane, etc. The short chain cyclic glycols offer the advantage of contributing to the cyclic character of the hard segment, thereby enhancing soft segment incompatibility and the likelihood of segmentation. Another type of diol that can be used in the invention is represented by Esterdiol 204 (Union Carbide). Hydroquinone bis(hydroxyethyl ether) is an advantageous extender with polyether polyols as the soft segment. In the most preferred case, however, the extender is 1,4 butanediol. The polymer properties tend to be superior when the extender hydroxyl groups are primary hydroxyl groups. The polyurethane may also be chemically cross-linked using a cross-linker which is built into the hard segment. In this case, the hard segment extender is a polyol such as trimethylol propane, glycerol, etc.

In making the polyurethane polymers, the extender, when present, is used in a molar ratio to the polyfunctional isocyanate of about 0.05 to 5.0 so as to provide a hard segment in the range of about 14 to about 25%. In terms of weight percent, the extender is usually used in an amount of about 0.5 to about 3.0% by weight. It is possible to control the degree of domain formation and physical cross-linking by adjusting the amount of extender.

The long chain diols useful in the present invention may be polyether diols or polyester diols and range in average molecular weight from approximately 500 to 5000 and preferably from 1000 to 3000. Some representative examples of the long chain polyester diols are polylactones such as polycaprolactone polyol, and copolymers of short chain diols and aliphatic dicarboxylic acids such as poly(ethylene adipate)polyol, poly(ethylene succinate)polyol, poly(ethylene sebacate)polyol, poly(butylene adipate)polyol, poly(ethylene butylene adipate)polyol, poly(diethylene ether adipate)polyol etc. The polyester polyols are preferably derived from short chain diols, preferably primary diols or mixtures of primary diols having 2-4 carbon atoms and an aliphatic dicarboxylic acid having 4 to 10 carbon atoms. The preferred polyester polyols are poly(ethylene butylane adipate)polyols with average molecular weights of about 2,000 to about 3,000. These polyols are commercially available from Ruco Polymer Corp., Hicksville, N.Y., under the trade name RUCOFLEX. The polycaprolactone polyols are available from Union Carbide, Danburry, Conn., under the trade name of TONE.

In addition to the aforementioned polyesters polyols, polyether polyols can also be used in the present invention. Two polyether polyols that have been used with some success are 1000 and 2000 average molecular weight poly(tetramethylene ether)glycols. These polyols are commercially available as Polymeg (Quaker Oats, Co., Chemical Division) and Teracol (du Pont) having various molecular weights.

Many long chain diols are crystalline at room temperature and/or may crystallize over time in the cured condom. To prevent this it is critical to use a mixture of long chain diols to depress the crystalline melting point of the polymer. The mixture may be one of different average molecular weight polyols or a mixture of chemically different polyols such as a mixture of polycaprolactone polyol and poly(ethylene adipate)polyol or poly(ethylene butylene adipate)polyol. For example, whereas a polymer containing solely polycaprolactone polyol as the soft segment undergoes a significant increase in modulus upon storage at 5° C. for only 10 days due to crystallization, polymers containing a mixed soft segment of polycaprolactone polyols and poly(ethylene adipate)polyols provide a relatively low and stable modulus at room temperature and at 5° C. The proportions of the polyesters making up the mixed soft segment will vary depending upon the nature of the polyesters used. Of course, some crystalline long chain diols (generally those having a crystalline melting points slightly above room temperature) do not crystallize in the polyurethane because in the polyurethane they are prevented by cross-linking from settling into a crystalline conformation or due to melting point depression which accompanies their incorporation into the polymer. Poly(ethylene butylene adipate)polyol is one such diol and is preferred for use in the present invention.

In the polyurethane condoms formed by the instant process, the percent hard segment and the degree of cross-linking in the polymer are adjusted for the diols used such that the polymer is essentially non-crystalline, i.e. amorphous, and has low set. It is also particularly desirable that the polyurethane films used in the present invention be essentially non-crystalline and non-crystallizable at temperatures of approximately 5° C. for at least four months. The latter requirement assures desirable storage stability and diol selection and degree of cross-linking are preferably adjusted to obtain this result.

One simple means of chemically cross-linking the invention polymers is to use a polyfunctional alcohol (i.e., compounds having three or more hydroxyl groups) in the polymer. Such compounds may be simple polyfunctional alcohols like trimethylolpropane or an adduct of a longer chain and a (short chain) polyfunctional alcohol. One that is often used is TONE POLYOL 0305 (an adduct of trimethylolpropane and Epsilon-caprolactone available from Union Carbide). In addition, other polyfunctional alcohols such as trimethylolethane and pentaerythritol can be used. Preferred cross-linking agents contain primary hydroxy groups.

One preferred example of a polyurethane used in the present invention is prepared by reacting MDI and 1,4-butanediol (as the hard segment component) and a mixture of poly(ethylene butylene adipate)polyol (2000 MW), and TONE POLYOL 0305.

The polyurethanes used in the present invention may be prepared in a conventional manner. For example, the diols (long chain diol, cross-linking agent and extender) are mixed and heated to about 50° C. To this mixture is added a melt of the polyisocyanate and then a polymerization catalyst. Alternatively, the catalyst can be added to the diols. Any of the metal salts of organic acids which are commonly used to catalyze polyurethane polymerizations, such as dibutyl tin dilaurate, can be used in the invention.

The prepolymers used in the present invention may be prepared by stopping the polymerization reaction which produces the low modulus polyurethanes at an intermediate stage. A number of conventional techniques may be employed for this purpose but one that has been found to be particularly useful on a condom production line is to add an end-blocking agent to the polyurethane reaction mixture. A particularly useful end-blocking agent is a heat-reversible end-blocking agent such as acetone oxime which can be removed to cure the prepolymer by merely heating to about 105° C. These prepolymers are formed using well known polyurethane polymerization catalysts such as dibutyl tin dilaurate. One procedure that is useful in preparing the prepolymers is disclosed in U.S. Pat. No. 3,846,378 to Griswold wherein a mixture of the diols, the cross-linking agent, and the end-blocking agent is prepared and the mixture is heated. To this mixture is added the diisocyanate followed by the polymerization catalyst. The reaction thereafter proceeds under its own reaction heat. The end-blocking agent is generally used in an amount equivalent to approximately 5 to 30% of the diisocyanate.

The solution coating compositions used in the aforementioned process are prepared by dissolving the polyurethane prepolymer in a suitable solvent. Many solvents can be used, but preferred solvents have a high solubility for the prepolymer, a low boiling point and low toxicity. One solvent that has been found particularly convenient for use in the invention is methylene chloride. Typical solution coating compositions containing approximately 25-40% by weight solids, 25-35% being preferred. These concentrations provide good film-forming viscosities. The polyurethane prepolymer solutions generally have a Brookfield viscosity of about 120 to about 470 CPS at 23° C. Generally, the prepolymer solution temperatures are kept between about 15° to about 25° C. to control viscosity and help prevent evaporation of the volatile solvent.

The condoms may be formed on commercially available porcelain or metallic forms in the present invention. Due to the high adhesion of the polyurethane, however, the forms must be surface treated to obtain adequate release properties. One treatment that can be used is to coat the forms with a release agent such as a silicone. Another technique is to use a specially prepared form having a surface of poly(tetrafluoroethylene). Other techniques conventionally used for mold release are also effective. To further enhance release, the polyurethanes used in the invention are preferably modified to incorporate a release agent such as a long chain silicone diol like Dow Corning's Q4-3667.

Appropriately prepared condom forms are dipped into the polyurethane prepolymer solution. The forms should be at a relatively cool temperature of about 15°-20° C. to prevent the volatile solvents, such as methylene chloride from evaporating too rapidly upon contact with the form. Unlike the dip-molding techniques involving emulsion technology, e.g., rubber latex dipping or polyurethane emulsion dipping, the polyurethane condoms formed by the instant invention do not depend on the use of a coagulation agent in the polyurethane solution. The condoms are then cured at elevated temperatures and lubricated with either a dry or wet lubricant. Starch powder is the preferred dry lubricant, although talc and other commonly used powder lubricants are useful. Petroleum jelly, silicone fluids or water soluble jelly lubricants may be used as a wet lubricant. The cured polyurethane condom is cooled to a temperature of about 50° C. to about 60° C., at which time an integral cuff is formed. Lubrication is applied subsequent to the formation of the integral cuff since it would otherwise prevent the cuff from adhering to the condom wall.

It may be desirable to employ a pigment which can be admixed with the polyurethane solution and co-deposited into the condom form therewith. Such conventional pigments as umber and $TiO_2$ can be used in the inventive process, but others well known to the art are contemplated. FD&C dyes such as yellow, green, blue, etc. are useful as well as long as they are dispersible and compatible with the prepolymer solution.

The following non-limiting examples further illustrate the invention. Unless otherwise indicated, all values are given in percent by weight.

EXAMPLE

This example is intended to show the criticality of process conditions and materials used in the instant process. Two polyurethane prepolymer formulations of the instant invention were prepared according to the procedure below and condoms were prepared therefrom. Formulations A & B are representative of the polyurethane prepolymer solutions of the instant invention. Formulations C, D & E are representative of polyurethane prepolymer solutions which have limited usefulness in the instant process because they do not produce condoms which are flexible enough and are of low enough modulus to be practical for consumer use. These comparison formulations are typical for the manufacture of polyurethane surgical gloves, where thickness of the glove ranges up to about 5 mils and more and where a slightly higher modulus is allowable.

All of the prepolymer formulations of Table I were prepared according to the following procedure.

A melted mixture of polycaprolactone triol (TONE 0305 polyol), polyester polyol, 1,4-butanediol, silicone polyol (Q4-3667) and acetone oxime was prepared by combining these ingredients at a temperature of about 50° C.-60° C. A separate mixture of the polyisocyanate and catalyst is prepared by melting about 45°-50° C. The polyisocyanate mixture is then added to the mixture containing the polyols and the reaction is allowed to proceed to completion at about 60°-90° C. Total reaction time varied according to the formulation but was generally between about 30 seconds and 2 minutes. Formulations containing HMDI as the polyisocyanate took a reaction time of about 3 minutes. Amounts of ingredients are recited in Table I.

Condom forms were fabricated from tubular aluminum stock to provide a form 11.5 inches in length, including a 0.7 inch reservoir tip. The form was wet sanded with a 600 wet/dry paper to provide a uniform, finely textured surface. Poly(tetrafluoroethylene) was applied to the form as a release agent to assist in removal of the condom once it is formed and cured on the form. The release-coated form is heated to cure the poly(tetrafluoroethylene).

The forms, thus being prepared for use, were then dipped into the respective polyurethane prepolymer solutions shown in Table I. Methylene chloride was used as the prepolymer solvent in all formulations. The withdrawal rate of the condom form in the prepolymer solution, as well as cure schedule and viscosity, are given in Table II. The condoms were then cooled, integral cuffs were rolled and the condoms were dusted with a starch powder.

Physical properties of the prepolymer solutions and the process parameters for each of the formulations are given in Table II.

Mechanical and physical properties of the polyurethane condoms formed via the instant process are shown in Tables III-IV.

As previously discussed, the choice of polyurethane prepolymer formulation is critical to the ultimate properties of the polyurethane condom and to the successful use of the instant process in making a commercially viable condom. The specific polyols or blend of polyols chosen must be non-crystalline, amorphous materials at ambient temperatures.

Formulations A & B, which are representative of those preferred for use with the instant process, meet this requirement. They use a blend of amorphous, non-crystalline polyols having melting points of about 23° C. Condoms made from the prepolymers which use these amorphous polyols are extremely flexible with low tensile modulus and high mechanical strength. (See Table III). These formulations can be contrasted with formulations C, D and E where the blend of polyols included at least one polyol which had more of a crystalline characteristic at ambient temperatures and whose melting point was about 55°-60° C. Condoms produced from these formulations via the instant process were less flexible and stiffer with a tensile modulus (Table III) higher than is desired for condoms.

Turning to Table III, the tensile modulus of the preferred formulations A and B are significantly lower at 100%, 300% and 500% than those values for C and D. Formulation E has relatively similar tensile modulus values as A&B. Formulation E does not, however, have the tensile strength, elongation, tensile set or tear properties of those formulations used in the instant invention (formulations A and B). Table III shows that the condoms formed using the instant process and particularly using formulations A and B have equal or better mechanical properties (tensile strength, set, elongation and tear) than the formulations used in the prior art polyurethane surgical glove making art, yet are more suitable for condoms due to their lower tensile modulus.

Turning to Table IV, a comparison of thicknesses is given of those polyurethane condoms of the instant process, using formulation A and commercially available latex condoms. As the table indicates, there is a wide variation of thickness and hence little uniformity in the latex condoms formed by conventional prior art techniques. The latex condom thickness deviates up to 2.3 mils. The latex condom, with the exception of sample IV, had the variation of greatest thickness at the tip of the condom. As previously discussed, this is a distinct disadvantage of the prior art condom process. The polyurethane condoms of the instant process exhibited more uniformity in thickness than the latex condoms with a deviation of at most 0.3 mils. The thickness at the tips of the polyurethane condoms was within 0.3 mil of the thickness at the condom base.

Table V demonstrates the excellent retention of physical properties of the preferred polyurethane formulation A after storage for indicated time periods. The importance of this data relates to shelf-life of the polyurethane condom which is necessary for a commercially viable product. As the table indicates, even at temperatures as low as 5° C., the soft, flexible properties of the condoms remained virtually the same after extended periods of time and differ little from those stored at 23° C.

TABLE I

Polyurethane Prepolymer Formulations

| Ingredient | Formulation - % by weight | | | | |
|---|---|---|---|---|---|
| | A | B | C | D | E |
| polycaprolactone triol (M.P. 15-20° C.) | 2.6 | 3.3 | 3.2 | 3.2 | 2.6 |
| polyester diol | | | | | |
| (a) M.W. 2,000, M.P. 23° C. | 41.5 | 39.2 | — | — | — |
| (b) M.W. 3,000, M.P. 23° C. | 31.5 | 32.8 | — | — | — |
| (c) M.W. 3,000, M.P. 30° C. | — | — | 30.5 | — | 32.7 |
| (d) M.W. 2,000, M.P. 55-65° C. | — | — | 43.1 | 60.2 | 40.5 |
| (e) M.W. 1,000, M.P. 55-65° C. | — | — | — | 7.6 | — |
| 1,4-butanediol | 1.9 | 1.9 | — | 2.2 | 1.8 |
| monoethanolamine | — | — | 1.1 | — | — |
| silicone polyol (Q4-3667) | 5.2 | 5.2 | 4.3 | 5.9 | 5.2 |
| acetone oxime | 1.4 | 1.6 | 1.5 | 1.6 | 1.4 |
| MDI | 15.9 | 16.0 | — | 19.3 | 15.8 |
| HMDI | — | — | 16.3 | — | — |
| % by weight Hard Segment | 17.3 | 18.4 | 17.4 | 21.5 | 17.6 |
| Mc (approx. M.W. between crosslinks) | 11,900 | 9,700 | 10,000 | 9,600 | 11,900 |

(a)-(c) represent amorphous poly(ethylene butylene adipate) diols (d)-(e) represent crystalline poly(ethylene adipate) diols

TABLE II

| | Formulation | | | | |
|---|---|---|---|---|---|
| | A | B | C | D | E |
| [1] concentration of prepolymer (in methylene chloride solvent) | 32 | 32 | 22 | 32 | 29 |
| Brookfield viscosity 23° C. Cps (optimum range) | 420-470 | 400-450 | 120-210 | 180-220 | 210-280 |
| Withdrawal Rate cm/min. | 1-25 | 16-25 | 56-89 | 16-25 | 20-33 |
| cure schedule | | | | | |
| Minutes | 30 | 30 | 30 | 30 | 20-30 |
| Temp. °C. | 150 | 150 | 175 | 175 | 150 |

[1] Total solids % weight

TABLE III

Mechanical Strengths of Polyurethane Condoms

| | Formulation | | | | |
|---|---|---|---|---|---|
| | A | B | C | D | E |
| Tensile Modulus, psi | | | | | |
| 10% | 40 | 40 | 50 | 50 | 40 |
| 100% | 120 | 150 | 160 | 160 | 120 |
| 300% | 200 | 270 | 320 | 320 | 200 |
| 500% | 380 | 570 | 760 | 790 | 410 |
| Tensile strength, psi (at break) | 4,000 | 4,600 | 3,100 | 4,400 | 3,000 |
| Elcoation, % (at break) | 810 | 640 | 540 | 710 | 710 |
| Tensile set, (% recovery) | | | | | |
| initial | 20 | 7 | 13 | 12 | 16 |
| 1 minute | 18 | 5 | 9 | 9 | 13 |
| Tear, pli | | | | | |
| slit | 24 | 16 | 50 | 22 | 23 |
| Die C | 80 | 120 | 130 | 98 | 84 |

TABLE IV

| | Condom Thickness (MILS)[3] | | | | |
|---|---|---|---|---|---|
| Distance from cuff- | | Latex Condoms[2] | | | |
| ring (inches) | PU Condom[1] | I | II | III | IV |
| (condom base) 1.0 | 2.4 | 2.1 | 1.9 | 1.8 | 3.0 |
| 2.0 | 2.4 | 2.3 | 2.0 | 2.0 | 3.0 |
| 3.0 | 2.5 | 2.5 | 2.0 | 2.0 | 3.0 |
| 4.0 | 2.4 | 2.7 | 2.2 | 2.1 | 3.0 |
| 5.0 | 2.5 | 3.0 | 3.0 | 2.8 | 2.7 |
| 5.5 | 2.5 | 3.1 | 3.1 | 3.1 | 2.9 |
| 6.0 | 2.5 | 3.8 | 3.5 | 3.2 | 2.9 |
| 6.5 | 2.7 | 4.2 | 3.5 | 3.6 | 2.9 |
| 7.0 | 2.7 | 4.2 | — | — | — |
| (condom reservoir tip) 7.5 | 26 | 3.6 | — | — | — |

(1) polyurethane condom made from prepolymer formulation A (TABLE I) using the instant process.
(2) Commercially available rubber latex condoms.

(3) Measurements for condom thickness were made at 90° C. intervals around the condom circumference, as well as at various intervals from the base to the reservoir tip as shown.

TABLE V

Physical Properties of Polyurethane Condom Formulation A after Storage

| Time at °C. | Tensile at break, psi | MODULUS | | | | % Elongation | Slit Tear | Tensile set % initial/1 min. |
|---|---|---|---|---|---|---|---|---|
| | | 10% | 100% | 300% | 500% | | | |
| 1 hr. @ 23° | 3900 | 40 | 120 | 170 | 260 | 930 | 40 | 40/30 |
| 4 days @ 23° | 3900 | 30 | 110 | 150 | 260 | 940 | 40 | 40/30 |
| 2 wks. @ 23° | 4000 | 40 | 110 | 160 | 270 | 940 | 30 | 40/30 |
| 1 mo. @ 23° | 4000 | 40 | 130 | 190 | 320 | 890 | 40 | 30/20 |
| 2 mos. @ 23° | 4100 | 40 | 120 | 180 | 340 | 840 | 40 | 20/20 |
| 4 mos @ 23° | 4100 | 40 | 120 | 190 | 350 | 850 | 40 | 20/20 |
| 8 mos @ 23° | 4100 | 40 | 120 | 190 | 370 | 850 | 40 | 20/20 |
| 2 wks. @ 5° | 3800 | 40 | 140 | 230 | 430 | 880 | 30 | 20/20 |
| 1 mo. @ 5° | 3800 | 40 | 150 | 220 | 400 | 860 | 40 | 20/20 |
| 2 mos. @ 5° | 3900 | 40 | 150 | 240 | 460 | 800 | 50 | 20/10 |
| 4 mos. @ 5° | 4000 | 40 | 150 | 260 | 510 | 790 | 50 | 20/20 |
| 8 mos. @ 5° | 4700 | 50 | 170 | 270 | 520 | 860 | 50 | 20/10 |

We claim:
1. Condoms consisting of a cross-linked thermoset polyurethane having a uniform wall thickness within the range of between about 2.2 and 2.8 mils obtained from a single dipping bath according to the process characterized by the steps of
   (a) setting up a single dipping bath, said bath comprising
      (1) a solvent solution of a polyurethane polymer or prepolymer;
      (2) said polymer or prepolymer being the reaction product of a polyisocyanate and at least one long chain polyol;
      (3) said polyol being amorphous and non-crystalline at room temperature and having an average molecular weight within the range of between about 500 and 6000;
      (4) said polyol having an average hydroxy number of within the range of between about 225 and 22.4; and
      (5) said polyisocyanate having an NCO/OH ratio of within the range of between about 0.95/1 and 1.1/1;
   (b) dipping molds on which condoms are to be formed in said single dipping bath for a period of time within the range of between about 30 and 60 seconds for depositing a polyurethane film in the form of a condom on each of said molds;
   (c) withdrawing said molds from said single dipping bath at the rate of within the range of between about 16 and 90 centimeters per minute;
   (d) curing said deposited film in the form of a condom on each of said molds by exposure to elevated temperatures for a time sufficient to effect said cure;
   (e) cooling the said cured film on said molds;
   (f) forming an integral cuff at the base of the said film on each of said molds; and
   (g) removing said deposited film in the form of a condom with an integral cuff from each of said molds.

2. Polyurethane condoms obtained by the process of claim 1, and further characterized by
   (a) said curing step being carried out for a period of time within the range of between about 20 and 40 minutes.

3. Polyurethane condoms obtained by the process of claim 1, further characterized by
   (a) said curing step being carried out at an elevated temperature within the range of between about 130 and 175 degrees Centigrade.

4. Polyurethane condoms obtained by the process of claim 1, further characterized by
   (a) said setting up step being carried out by providing said bath with a Brookfield viscosity within the range of between about 120 and 470 centipoise.

5. Polyurethane condoms obtained by the process of claim 1, further characterized by
   (a) prior to said dipping step selecting molds on which said condoms are to be formed;
   (b) applying in a first applying step a textured surface to said molds from said selecting step; and
   (c) applying in a second applying step a release agent to said textured surfaces.

6. Polyurethane condoms obtained by the process of claim 1, further characterized by
   (a) said second applying step being carried out with polytetrafluoroethylene powder.

7. Polyurethane condoms obtained by the process of claim 1, further characterized by
   (a) said cooling step being carried out to a temperature within the range of between about 50 and 60 degrees Centigrade.

8. Condoms comprised of a cross-linked thermoset polyurethane having a uniform wall thickness within the range of between about 2.2 and 2.8 mils obtained from a single dipping bath according to the process characterized by the steps of
   (a) setting up a single dipping bath, said bath comprising
      (1) a solvent solution of a polyurethane polymer or prepolymer;
      (2) said polymer or prepolymer being the reaction product of a polyisocyanate and at least one long chain polyol;
      (3) said polyol being amorphous and non-crystalline at room temperature and having an average molecular weight within the range of between about 500 and 6000;
      (4) said polyol having an average hydroxy number of within the range of between about 225 and 22.4; and
      (5) said polyisocyanate having an NCO/OH ratio of within the range of between about 0.95/1 and 1.1/1;

(b) dipping molds on which condoms are to be formed in said single dipping bath for a period of time within the range of between about 30 and 60 seconds for depositing a polyurethane film in the form of a condom on each of said molds;

(c) withdrawing said molds from said single dipping bath at the rate of within the range of between about 16 and 90 centimeters per minute;

(d) curing said deposited film in the form of a condom on each of said molds by exposure to elevated temperatures for a time sufficient to effect said cure;

(e) cooling the said cured film on said molds;

(f) forming an integral cuff at the base of the said film on each of said molds;

(g) applying a lubricant to said deposited film in the form of condoms;

(h) said lubricant being a member selected from the group consisting of starch, a silicone compound or a water soluble gel lubricant; and (i) removing said deposited film in the form of a condom with an integral cuff from each of said molds.

* * * * *